United States Patent
Foreman et al.

(10) Patent No.: US 8,814,826 B2
(45) Date of Patent: Aug. 26, 2014

(54) SEQUENTIALLY INFLATABLE BALLOONS FOR DELIVERY OF TREATMENT AGENTS

(75) Inventors: Philip C. Foreman, San Jose, CA (US); Katsuyuki Murase, Cupertino, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1176 days.

(21) Appl. No.: 11/696,655

(22) Filed: Apr. 4, 2007

(65) Prior Publication Data

US 2008/0249461 A1 Oct. 9, 2008

(51) Int. Cl.
*A61M 29/00* (2006.01)

(52) U.S. Cl.
USPC .............. 604/96.01; 604/101.01; 604/101.04; 604/101.05; 604/915; 604/919

(58) Field of Classification Search
USPC ............... 604/101.01, 101.03, 101.05, 93.01, 604/96.01, 101.02, 264, 523, 912, 915–921
See application file for complete search history.

(56) References Cited

U.S. PATENT DOCUMENTS

| | | | | |
|---|---|---|---|---|
| 4,066,070 A | * | 1/1978 | Utsugi | 600/116 |
| 4,423,725 A | * | 1/1984 | Baran et al. | 128/207.15 |
| 4,546,759 A | * | 10/1985 | Solar | 600/18 |
| 5,019,042 A | * | 5/1991 | Sahota | 604/101.01 |
| 5,395,333 A | * | 3/1995 | Brill | 604/101.05 |
| 5,765,559 A | * | 6/1998 | Kim | 128/207.15 |
| 5,782,740 A | * | 7/1998 | Schneiderman | 600/1 |
| 5,800,393 A | * | 9/1998 | Sahota | 604/103.07 |
| 5,820,595 A | * | 10/1998 | Parodi | 604/101.05 |
| 5,876,426 A | * | 3/1999 | Kume et al. | 607/88 |
| 6,148,222 A | * | 11/2000 | Ramsey, III | 600/380 |
| 6,258,019 B1 | * | 7/2001 | Verin et al. | 600/1 |
| 6,527,739 B1 | * | 3/2003 | Bigus et al. | 604/101.01 |
| 2002/0099332 A1 | * | 7/2002 | Slepian et al. | 604/96.01 |
| 2006/0129093 A1 | * | 6/2006 | Jackson | 604/96.01 |

FOREIGN PATENT DOCUMENTS

DE 200 06 443 U1 10/2000

OTHER PUBLICATIONS

PCT International Search Report and Written Opinion for International Application No. PCT/US2008/003976, mailed Jul. 23, 2008 (15 pages).

* cited by examiner

*Primary Examiner* — Kami A Bosworth
*Assistant Examiner* — Imani Hayman
(74) *Attorney, Agent, or Firm* — Randy Shen; Blakely Sokoloff Taylor & Zafman LLP

(57) ABSTRACT

An apparatus including a cannula having a dimension suitable for insertion into a blood vessel and an expandable body coupled thereto, the expandable body comprising a first expandable member and a second expandable member to isolate a length of the vessel upon expansion within the blood vessel. The expandable body having an intermediate expandable member along a working length between the first expandable member and the second expandable. A method including introducing a cannula and an expandable body coupled thereto into a blood vessel at a point coextensive with a treatment site and expanding a first expandable member and a second expandable member of the expandable body to isolate a length of the vessel adjacent the treatment site. The method further including delivering a treatment agent to a vessel region between the first expandable member and the second expandable member while inflating and deflating an intermediate expandable member.

9 Claims, 8 Drawing Sheets

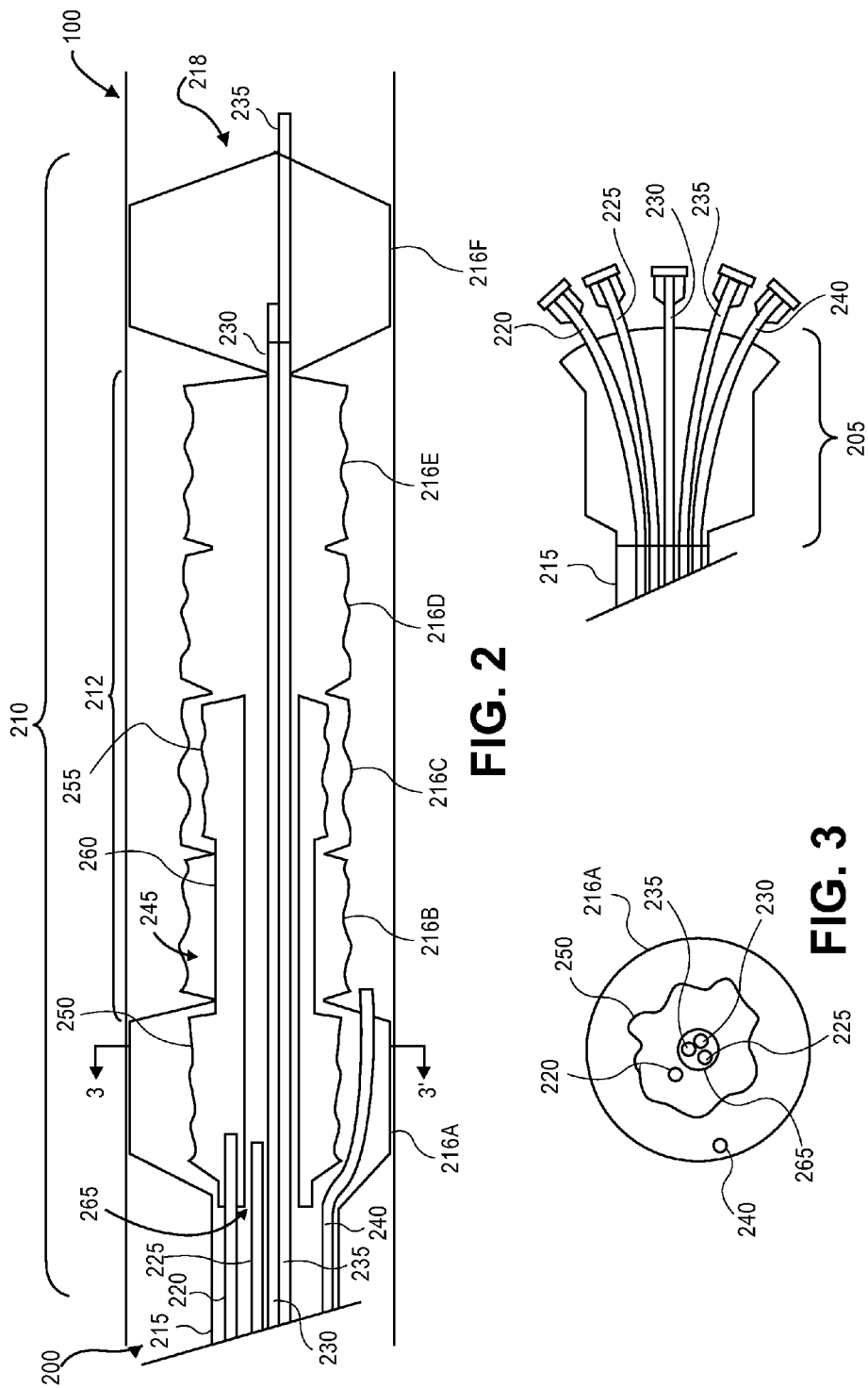

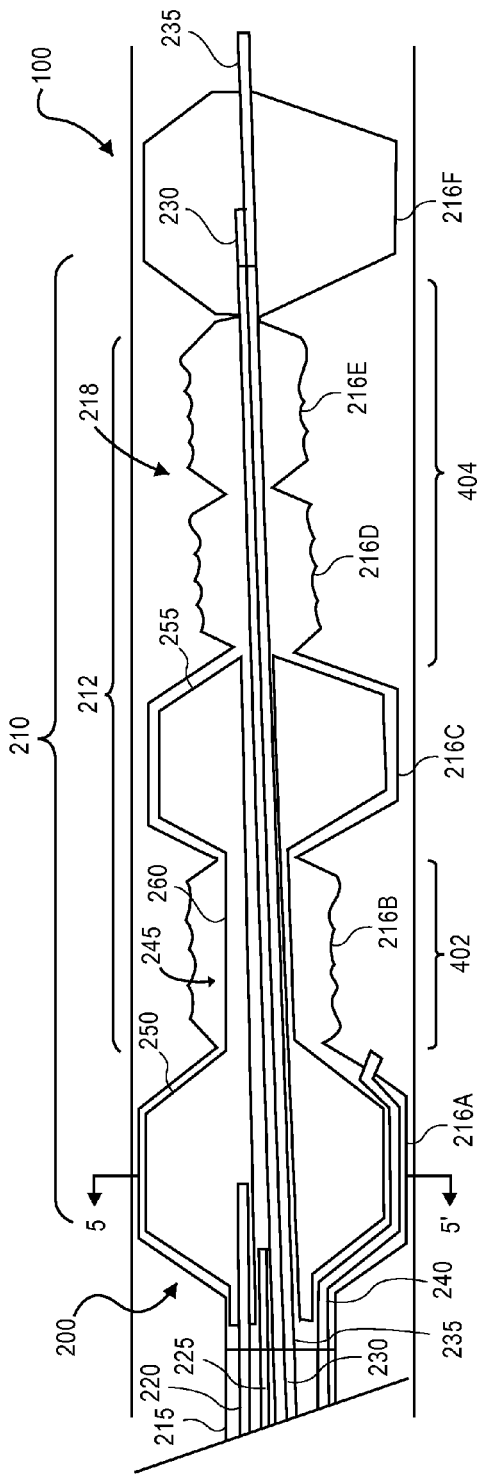
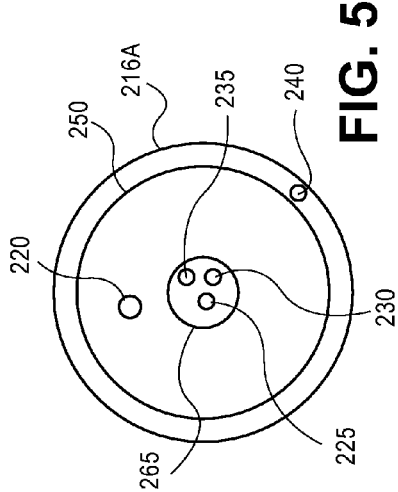
FIG. 4
FIG. 5

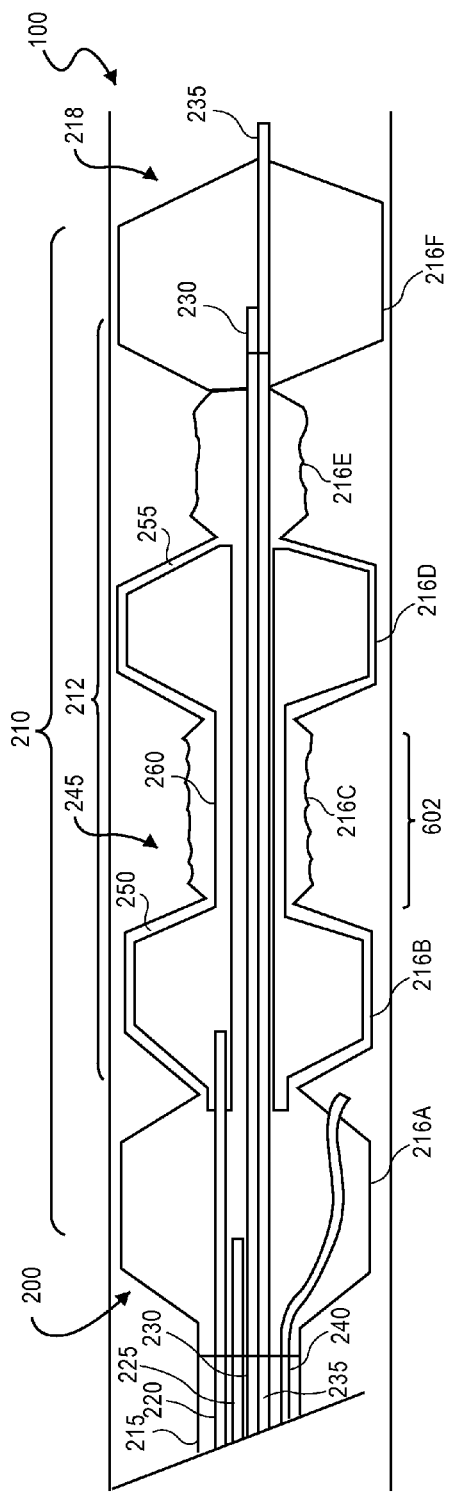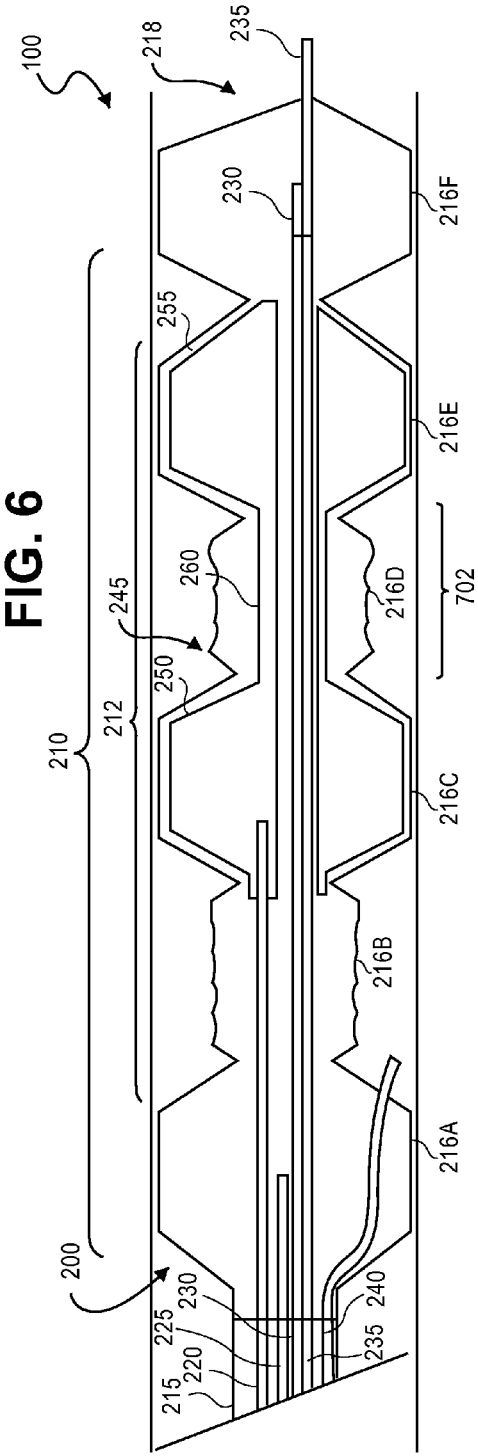

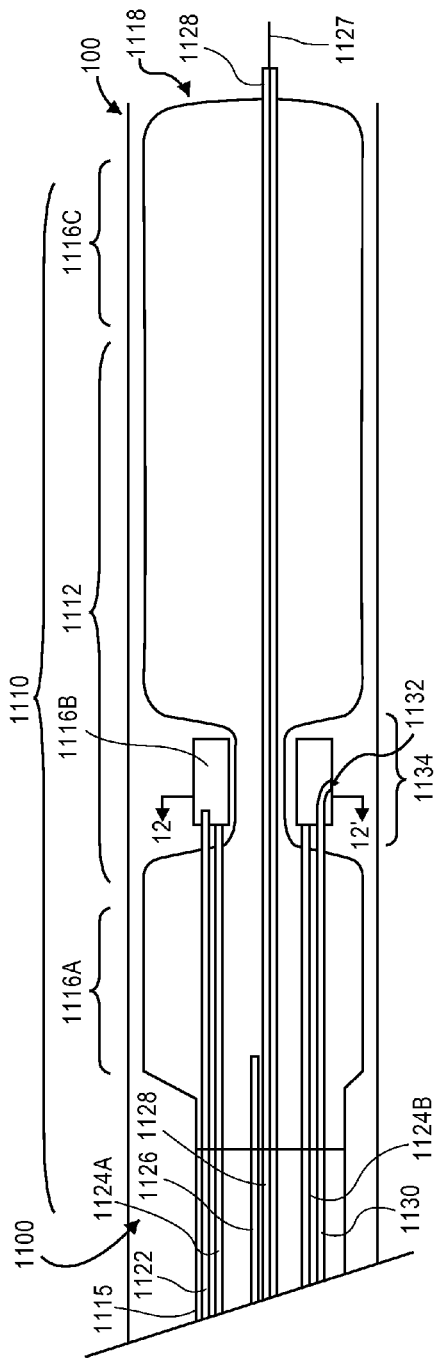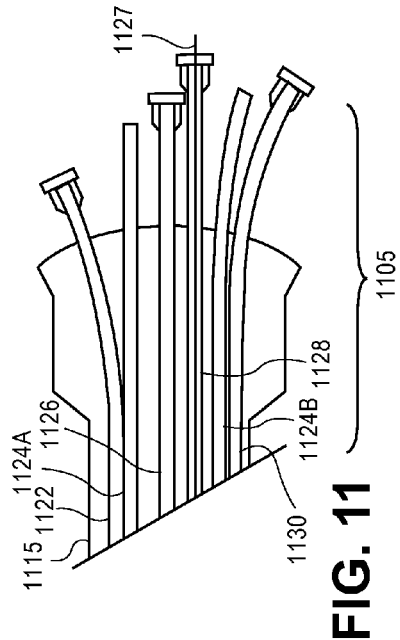
FIG. 11
FIG. 12

SEQUENTIALLY INFLATABLE BALLOONS FOR DELIVERY OF TREATMENT AGENTS

FIELD

Methods and devices for delivering a treatment agent to a vessel.

BACKGROUND

Balloon angioplasty is utilized as an alternative to bypass surgery for treatment early in the development of stenosis or occlusion of blood vessels due to the abnormal build-up of plaque on the endothelial wall of a blood vessel. Angioplasty typically involves guiding a catheter that is usually fitted with a balloon through an artery to the region of stenosis or occlusion, followed by brief inflation of the balloon to push the obstructing intravascular material or plaque against the endothelial wall of the vessel, thereby compressing and/or breaking apart the plaque and reestablishing blood flow. In some cases, particularly where a blood vessel may be perceived to be weakened, a stent can be deployed following an angioplasty procedure to support the vessel.

Balloon angioplasty and stent deployment, however, can result in injury to a wall of a blood vessel and its endothelial lining. For example, undesirable results such as denudation (removal) of the endothelial cell layer in the region of the angioplasty, dissection of part of the inner vessel wall from the remainder of the vessel wall with the accompanying occlusion of the vessel, or rupture of the tunica intima layer of the vessel may occur. A functioning endothelial reduces or mitigates thrombogenicity, inflammatory response, and neointimal proliferation.

To reduce or treat injury to the vessel wall, angioplasty balloons and stents may further be used to deliver treatment agents to the targeted vessel regions. The use of angioplastly balloons and stents to deliver treatment agents, however, may be limited by the type of drug being delivered. In addition, stents can undesirably increase the profile and stiffness of a delivery system, affect drug distribution and require a high-pressure angioplasty balloon for deployment.

SUMMARY

According to one embodiment, techniques described herein are used to inhibit vascular smooth muscle cell proliferation or restenosis following, for example, vascular intervention or injury, or in denuded or incompletely endothelialized areas of vasculature. The techniques are also used for other treatment approaches, such as stabilization of atherosclerotic plaque, facilitation of reverse cholesterol efflux as well as endothelialization. In some embodiments, this is achieved by isolating a vessel region at risk for restenosis and reducing the blood volume within this region. Once the region is isolated, a treatment agent, for example, an immunosuppressive agent which inhibits the proliferation of vascular smooth muscle cells (e.g. everolimus), is delivered to the isolated vessel region. Since the treatment agent is isolated to a specific region, the risk of side effects caused by a treatment agent traveling to an undesired vascular or tissue region is reduced. In addition, reducing the blood volume within the region of treatment agent delivery prevents dilution of the treatment agent solution at the treatment site. In this aspect, the concentration of treatment agent delivered is maintained at the treatment site, and after the treatment, the agent may be removed by inflating a balloon to minimize systemic exposure of the treatment agent. In still further embodiments, a pressure within the region is controlled by the intermediate expandable member in order to achieve a suitable local pressure to drive the treatment agent through the vessel wall.

According to one embodiment, the treatment agent is delivered to a desired treatment site within a lumen of a blood vessel by positioning a cannula having a dimension suitable for insertion into a blood vessel and an expandable body coupled thereto adjacent to the treatment site. The expandable body includes a first expandable member and a second expandable member to isolate a length of the vessel upon expansion. In some embodiments, the first and second expandable members are selectively inflatable balloons. In addition to isolating a vessel region, expansion of the first and second expandable members holds the expandable body in place. The expandable body further includes a working length between the first expandable member and the second expandable member. The working length includes at least one intermediate expandable member. In some embodiments, the intermediate expandable member is a balloon which is selectively inflated and deflated. The intermediate expandable member may be inflated between the first and second expandable members to reduce a blood volume within the isolated region. Still further, the expansion of the intermediate member increases a pressure within the isolated vessel region thus when inflated after a treatment agent has been introduced into this region, the expansion helps to drive a treatment agent through the vessel wall. In still further embodiments, there is more than one intermediate expandable member. In this embodiment, the intermediate expandable members are selectively inflated and deflated along the working length to further isolate segments of the vessel between the first and second expandable members and in turn the treatment agent within these segments.

According to another embodiment, a method is described. The method includes introducing a cannula having a dimension suitable for insertion into a blood vessel and an expandable body coupled thereto into a blood vessel at a point coextensive with a treatment site. Once in position, a first expandable member, and a second expandable member of the expandable body are inflated to isolate a length of the vessel adjacent the treatment site. In some embodiments, a treatment agent is then delivered to the isolated vessel region and an intermediate expandable member is inflated to adjust a pressure of a vessel region within the isolated region which, in turn, drives the treatment agent through the vessel wall. In some embodiments, multiple intermediate expandable members between the first and second expandable members are selectively inflated and deflated. In this aspect, the intermediate expandable members are inflated and deflated independent of one another according to a peristaltic motion such that segments of the vessel between the first and second expandable members may further be isolated to control distribution of the treatment agent along the vessel.

In other embodiments, the first expandable member, the intermediate expandable member, and the second expandable member are simultaneously inflated prior to delivery of the agent to drive a volume of blood out of the vessel region between the first expandable member and the second expandable member. The intermediate member is then deflated and a treatment agent is delivered to the vessel region between the first expandable member and the second expandable member. The intermediate member is then re-inflated to adjust a pressure within the isolated vessel region and drive the treatment agent through the vessel wall.

As used herein, treatment agents include, but are not intended to be limited to, drugs, biologically active agents, chemically active agents, therapeutic agents, and the like, and pharmaceutical compositions thereof, which can be used to deliver a treatment agent to a treatment site as described herein. In some embodiments, the treatment agent may be an agent suitable for local treatment, regional treatment or a combination of agents suitable for local and regional treatment. For example, the treatment agent may be a combination of anti-inflammatory and anti-proliferative agents. In still further embodiments, the treatment agent is an agent that would benefit a damaged blood vessel or an infarcted area. Still further, a contrast agent may be delivered from the delivery outlets in combination with, or in addition to, a treatment agent.

According to another embodiment, a kit is described. The kit includes a cannula of a dimension suitable for insertion into a blood vessel and an expandable body coupled thereto. The expandable body includes a first expandable member and a second expandable member to isolate a length of the vessel upon expansion. The expandable body further includes a working length between the first expandable member and the second expandable member comprising at least one intermediate expandable member. The kit further includes a treatment agent for delivery to a treatment site along a length of vessel between the first expandable member and the second expandable member.

BRIEF DESCRIPTION OF THE DRAWINGS

FIG. 2 shows a cross-sectional side view of an embodiment of a catheter assembly to deliver a treatment agent introduced into the blood vessel.

FIG. 3 shows a cross-sectional front view of the catheter assembly of FIG. 2.

FIG. 4 shows the catheter assembly of FIG. 2 with an intermediate expandable member of the catheter assembly inflated.

FIG. 5 shows a cross-sectional front view of the catheter assembly of FIG. 4.

FIG. 6 shows the catheter assembly of FIG. 2 with two intermediate expandable members of the catheter assembly inflated.

FIG. 7 shows the catheter assembly of FIG. 2 with two intermediate expandable members of the catheter assembly inflated.

FIG. 11 shows a cross-sectional side view of another embodiment of a catheter assembly to deliver a treatment agent introduced into the blood vessel.

FIG. 12 shows a cross-sectional front view of the catheter assembly of FIG. 11.

DETAILED DESCRIPTION

Figure 1:
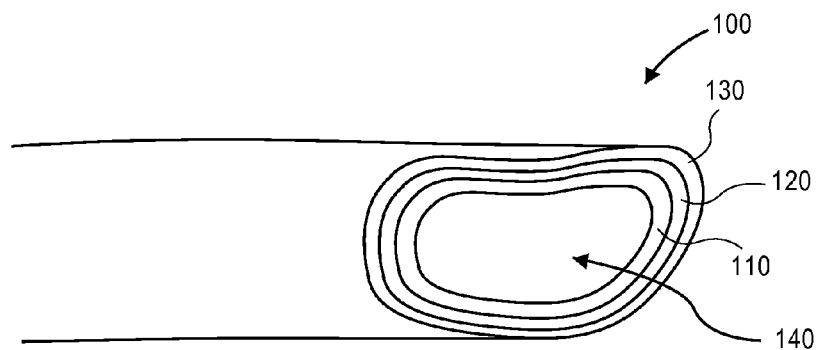
FIG. 1 shows a schematic side and sectional view of a blood vessel.

Referring to FIG. 1, a non-diseased artery is illustrated as a representative blood vessel. Blood vessel 100 includes an arterial wall having a number of layers. Inner most layer 110 is generally referred to as the intimal layer that includes the endothelium, the subendothelial layer, and the internal elastic lamina. Medial layer 120 is concentrically outward from inner most layer 110 and bounded by external elastic lamina. There is no external elastic lamina in a vein. Medial layer 120 (in either an artery or vein) primarily consists of smooth muscle fibers and collagen. Adventitial layer 130 is concentrically outward from medial layer 120. The arterial wall (including inner most layer 110, medial layer 120 and adventitial layer 130) defines lumen 140 of blood vessel 100. Stenosis or occlusion of a blood vessel such as blood vessel 100 occurs by the build-up of plaque on inner most layer 110. The stenosis or occlusion can result in decreased blood flow through lumen 140. As previously discussed, one technique to address this is angioplasty and stent deployment. Balloon angioplasty and stent deployment, however, may result in injury to blood vessel 100 and its endothelial lining, resulting in a potential formation of thrombus or neointimal proliferation. A functioning endothelial reduces or mitigates thrombogenecity, inflammatory response, neointimal proliferation. Therefore, it is desirable to treat the injured vessel region so that the risk of, for example, restenosis is reduced.

Treatment Agents

A treatment agent as used herein includes any type of agent suitable for treating a desired tissue region. In one embodiment, the treatment agent is a growth factor (e.g. insulin-like growth factor 1), small peptide or drug which facilitates tissue repair when delivered to a desired treatment site. A treatment agent may further include agents that promote angiogenesis (angiogenesis promoting factors), agents that promote cell survival (cell survival promoting factors), and agents that recruit endogenous progenitor or stem cells (endogenous recruiting factors) for treatment of post-myocardial infarction.

In some embodiments, the treatment agent is an agent that would benefit a blood vessel or an infarcted area (e.g., tissue) by itself creating new cells or new cell components or trigger a repair mechanism. For example, the treatment agent can include endothelial cells, stem cells or progenitor cells (e.g., endothelial progenitor cells) that will repopulate an injured vessel wall and/or stent (or other blood contacting implant) surface when delivered to an injured tissue region. A treatment agent may also include an agent that benefits a blood vessel or an infarcted area (e.g., tissue) only with the assistance of another exogenous or endogenous agent. In this aspect, suitable treatment agents may include, but are not limited to, growth factors (e.g., vascular endothelial growth factor (VEGF), fibroblast growth factor (FGF), platelet-derived growth factor (PDGF)), cellular components, proteins, cytokines, and drugs. Still further, the treatment agent may include a bioactive agent used to induce regression or slow progress of an atherosclerotic plaque, such as apolipoprotein A1 (Apo A1) or a mutant or mimic form of Apo A1, or a molecule mimicking the cholesterol transporting capacity of Apo A1.

In other embodiments, the treatment agent is an anti-inflammatory agent. Examples include, but are not limited to, mometasone, clobetasol and dexamethasone. In another embodiment, the treatment agent is an anti-proliferative or immunosuppressive agent. Examples of such agents include, but are not limited to, sirolimus, everolimus, zotarolimus, and paclitaxel. In another embodiment, the treatment agent may be a combination of anti-inflammatory and anti-proliferative agents. In other embodiments, the treatment agent is an antioxidation agent. Examples include, but not limited to, tocopherol, probucol, and superoxide dismutase (SOD). The treatment agent may also include DNAs, RNAs in order to express or suppress certain genes to achieve therapeutic goals described above.

The treatment agent may be delivered to a target region in the form of a solution or formulation. Representatively, the solution may be a saline buffer solution and one or more treatment agents. The amount of each agent in solution may be any amount suitable for treating the desired vessel region.

In some embodiments, the treatment agent may be packaged or encapsulated in a carrier. A carrier can include a matrix that contains one or more treatment agents. A suitable carrier may take the form of a nanoparticle (e.g., nanosphere), microparticle (e.g., microsphere), liposome, micelle, polyplex and the like particles, as the situation may dictate. For example, the carrier may be a liposome or other outer shell such as, for example, lipid or polymer membranes, polymer shells, or other lipid-philic shells. A suitable material for the carrier can be a polypropylene sulfide (PPS).

In one exemplary embodiment, a formulation including a treatment agent encapsulated in a carrier may include everolimus encapsulated in PPS nanoparticles of 100 nanometer diameter and ApoA1 encapsulated in a 1,2-distearoyl phosphatidylcholine (DSPC)-based liposome. A medium for the carrier may be PBS or 0.05% Hyaluronic acid in phosphate-buffered saline (PBS).

Devices

The following paragraphs describe representative devices that are used to introduce any of the foregoing treatment agents to a desired treatment site.

To increase diffusion of a treatment agent to a desired vessel region, blood flow may be temporarily reduced or stopped within the desired region by occluding the target vessel prior to the introduction of the treatment agent. FIG. 2 shows blood vessel 100 having catheter assembly 200 disposed therein. Catheter assembly 200 includes proximal portion 205 and distal portion 210. Proximal portion 205 is external to blood vessel 100 and to the patient. Representatively, catheter assembly 200 may be inserted through a femoral artery and through, for example, a guide catheter and with the aid of a guidewire to a location in the vasculature of a patient. In some embodiments, that location is a coronary artery. FIG. 2 shows distal portion 210 of catheter assembly 200 positioned along a length of vessel 100.

In one embodiment, catheter assembly 200 includes primary cannula 215 having a length that extends from proximal portion 205 (e.g., located external through a patient during a procedure) to distal portion 210. One end of primary cannula 215 connects to a proximal end of expandable body 218. Expandable body 218 includes a plurality of sequentially positioned expandable members 216a, 216b, 216c, 216d, 216e and 216f. Although six expandable members are illustrated in FIG. 2, it is contemplated that any multiple number of expandable members capable of allowing expandable body 218 to expand and contract in a peristaltic like motion may be used. For example, in some embodiments, three intermediate expandable members may be provided. A "peristalsis" or "peristaltic" motion as used herein generally refers to a progressive wave like motion of expandable body 218 which occurs along its length to isolate vessel regions. For example, in some embodiments, expandable members 216a, 216b, 216c, 216d, 216e and 216f are balloons. In this aspect, a peristaltic motion may be achieved by expanding balloons 216b and 216d, followed by contraction of balloon 216b, expansion of balloon 216c, contraction of balloon 216d and expansion of balloon 216e. This motion may continue until an end of expandable body 218 is reached. Alternatively, expandable body 218 may include any type of expandable member capable of producing a peristaltic like motion along a length of expandable body 218.

Balloons 216a, 216b, 216c, 216d, 216e and 216f may be of the same or different materials. In some embodiments, end balloons 216a and 216f are used to occlude vessel 100 and anchor expandable body 218 in place within vessel 100. In this aspect, balloons 216a and 216f are made of a material suitable for anchoring expandable body 218 within vessel 100, such as an elastomeric material, while balloons 216b, 216c, 216d and 216e may be made of a different, e.g., less compliant, material. Suitable materials include, but are not limited to, non-permeable materials such as Pebax®, nylon or polyethylene terephthalate (PET). Alternatively, balloons 216a, 216b, 216c, 216d, 216e and 216f are made of a porous material such as extended polytetrafluoroethylene (ePTFE). In some embodiments, balloons 216a, 216b, 216c, 216d, 216e and 216f are formed together, by for example, a blow-molding process of a single seamless material capable of forming the sequential balloon configuration shown in FIG. 2. Alternatively, balloons 216a, 216b, 216c, 216d, 216e and 216f may be formed separately and then bonded together at their ends. Regardless of the technique used for forming balloons 216a, 216b, 216c, 216d, 216e and 216f, it is desired that a passageway be maintained from one end of expandable member 218 to another to allow a cannula and, in some embodiments, expansion mechanism 245, to pass through each of the balloons along the length of expandable body 218. In this aspect, end balloons, for example, 216a and 216f, may be inflated and deflated independent of the intermediate balloons and used to anchor expandable body 218 within the vessel lumen. For example, one inflation cannula may extend to balloon 216a to allow inflation of balloon 216a and a separate inflation cannula may extend to balloon 216f to allow the separate inflation of balloon 216f.

A size and shape of balloons 216a, 216b, 216c, 216d, 216e and 216f may vary. Although, substantially tubular balloons with a circular cross-section are illustrated in FIG. 2, it is contemplated that the balloons may be conical, tapered, stepped or of any other shape deemed desirable. A suitable balloon diameter is, for example, in the range of two to five millimeters (mm). A balloon length may be on the order of eight to 60 mm. A suitable balloon profile range is, for example, approximately 0.030 inches to 0.040 inches.

Primary cannula 215 connects with a proximal end or skirt of balloon 216a. Primary cannula 215 has a lumen therethrough dimensioned to accommodate inflation cannulas 220, 225, 230, guidewire cannula 235 and delivery cannula 240 therein. Inflation cannula 220 extends from proximal portion 205 of catheter assembly 200 to distal portion 210 and has an end that terminates within expansion mechanism 245 positioned within expandable body 218. Inflation cannulas 225 and 230 extend from proximal portion 205 to distal portion 210 and have ends that terminate within balloons 216a and 216f, respectively. In this aspect, balloons 216a and 216f may be inflated and in turn used to occlude vessel 100 by delivering, for example, a fluid, through inflation cannulas 225 and 230 to balloons 216a and 216f, respectively. In one embodiment, balloons 216a and 216f have a dimension such that each balloon may be inflated to a diameter suitable to occlude vessel 100 without causing damage to the vessel wall.

Delivery cannula 240 extends from proximal portion 205 of catheter assembly 200 to distal portion 210. Delivery cannula 240 extends through balloon 216a and terminates outside of balloon 216a within the vessel region between balloons 216a and 216f to allow for delivery of a treatment agent to the region between expandable member 216a and 216f. Although delivery cannula 240 is shown, it is further contemplated that other mechanisms suitable for delivering a treatment agent to the region between balloons 216a and 216f may be used as deemed desirable.

Catheter assembly 200 also includes guidewire cannula 235 extending, in this embodiment, through expandable body 218 to a distal end of catheter assembly 200 to facilitate insertion of catheter assembly 200 into vessel 100. Guidewire cannula 235 has a lumen sized to accommodate a guidewire (not shown). Catheter assembly 200 may be an over the wire (OTW) configuration where guidewire cannula 235 extends from a proximal end (external to a patient during a procedure) to a distal end of catheter assembly 200. In some embodiments, guidewire cannula 235 may also be used for delivery of a treatment agent to a region upstream from catheter assembly 200 when the guidewire is removed with catheter assembly 200 in place.

In another embodiment, catheter assembly 200 is a rapid-exchange-type (RX-type) catheter assembly and only a portion of catheter assembly 200 (a distal portion including expandable body 218) is advanced over the guidewire. In an RX-type of catheter assembly, typically, the guidewire cannula extends from the distal end of the catheter to a proximal guidewire port spaced distally from the proximal end of the catheter assembly. The proximal guidewire port is typically spaced a substantial distance from the proximal end of the catheter assembly.

In one embodiment, catheter assembly 200 includes expansion mechanism 245 to selectively expand or contract expandable members 216b, 216c, 216d and 216e. In some embodiments, expansion mechanism 245 is further used to expand or contract expandable member 216a or 216f. Expandable mechanism 245 includes balloon 250 and balloon 255 at opposite ends of secondary cannula 260. A proximal portion or skirt of balloon 255 connects to a distal end of secondary cannula 260. A distal end or skirt of balloon 250 is connected to a proximal end of secondary cannula 260. Balloons 250 and 255 may be of any material, for example, an elastomeric material similar to that which may be used for expandable members 216b, 216c, 216d and 216e, capable of supporting an overlying balloon structure upon inflation. Secondary cannula 260 may be of the same or slightly less compliant material than that of balloons 250 and 255. Secondary cannula 260 has a length dimension, in one embodiment, suitable to extend a length of one of balloons 216b, 216c, 216d and 216e. In this embodiment, secondary cannula 260 has a property such that it may be inflated to a diameter greater than its outside diameter when it is introduced into vessel 100 (in other words, secondary cannula 260 is made of an expandable material).

FIG. 2 shows a single inflation cannula 220 terminating within balloon 250 to expand each of balloon 250, secondary cannula 260 and balloon 255. In this aspect, a fluid or gas may be delivered through inflation cannula 220 to inflate (i.e., expand) expansion mechanism 245 or withdrawn to deflate (i.e., contract) expansion mechanism 245. In another embodiment, separate inflation cannulas are used to expand each of balloon 250, secondary cannula 260 and balloon 255. Channel 265 is formed through expansion mechanism 245. Channel 265 is dimensioned to allow expansion mechanism 245 to be positioned around inflation cannula 230 and guidewire cannula 235 so that expansion mechanism 245 can slide over inflation cannula 230 and guidewire cannula 235. In this aspect, expansion of expansion mechanism 245 at different positions within expandable body 218 produces a peristaltic action via balloons 216b, 216c, 216d and 216e along working length 212. Although a balloon type expansion mechanism is illustrated in FIG. 2, it is contemplated that any type of expansion mechanism suitable for selectively expanding or contracting balloons 216b, 216c, 216d and 216e may be used. Suitable mechanisms may include, but are not limited to, an electrically controlled expansion mechanism or valve type expansion mechanism.

In one embodiment, catheter assembly 200 is introduced into blood vessel 100 and balloons 216a and 216f are inflated (e.g., with a suitable liquid through inflation cannulas 225 and 230) to occlude blood vessel 100 and isolate a vessel region adjacent working length 212. In some embodiments, balloons 216a and 216f are positioned on opposite sides of a treatment site to isolate the treatment site prior to delivery of the treatment agent. During insertion of catheter assembly 200 into vessel 100, expansion mechanism 245 is positioned in an unexpanded state within catheter assembly 200 such that balloon 250 is within balloon 216a, secondary cannula 260 is within balloon 216b and balloon 255 is within balloon 216c. Following occlusion, a solution (fluid) of the treatment agent is introduced through delivery cannula 240 to the isolated vessel region.

FIG. 3 shows a cross-sectional front view of the catheter assembly of FIG. 2 at 3-3'). In this embodiment, a cross-sectional front view through line 3-3' of balloon 216a is shown. Balloon 250 is positioned within balloon 216a in an unexpanded state. Delivery cannula 240 is positioned within balloon 216a. Inflation cannulas 225 and 230 and guidewire cannula 235 are positioned through cavity 265 of balloon 250. In this embodiment, balloon 250 is not yet inflated thereby allowing a treatment agent to be delivered through delivery cannula 240 positioned between walls of balloon 250 and balloon 216a.

Once the treatment agent is delivered, expansion mechanism 245 is inflated as illustrated in FIG. 4 to further isolate a region 402 between balloons 216a and 216c. Catheter assembly 200 having the same components as described in reference to FIG. 2 is shown in FIG. 4 with balloon 255 expanding balloon 216c. Secondary cannula 260 is expandable to an outside diameter less than an expanded outside diameter of balloon 216a or balloon 216c (e.g., secondary cannula 260 has an inflated diameter less than an inner diameter of blood vessel 100 at a treatment site). In this aspect, balloon 216b adjacent secondary cannula 260 remains in an unexpanded state. Balloon 255 is inflated to a dimension suitable to retain an amount of the treatment agent within region 402 and increase a pressure within this region. Balloon 216f remains in an expanded state thus it is further contemplated that a pressure within region 404 of blood vessel 100 between balloon 216c and balloon 216f may be increased. The pressure increase within these regions helps to drive the treatment agent through walls of vessel 100.

FIG. 5 shows a cross-sectional front view of the catheter assembly of FIG. 4. Similar to FIG. 3, a cross-sectional front view through balloon 216a is shown (at 5-5'), in this embodiment, however, balloon 250 is positioned within balloon 216a in an expanded state. In this aspect, delivery cannula 240 is positioned between walls of balloon 250 and balloon 216a. In some embodiments, the expansion of balloon 250 pinches delivery cannula 240 between a wall of balloon 250 and balloon 216a and closes off delivery cannula 240 such that the treatment agent may no longer be delivered through delivery cannula 240. Inflation cannulas 225 and 230 and guidewire cannula 235 are positioned through cavity 265 of balloon 250.

FIG. 6 shows the catheter assembly of FIG. 2 with two intermediate expandable members of catheter assembly 200 expanded. In this embodiment, expansion mechanism 245 is repositioned from that which is shown in FIG. 4 so that balloon 250 is positioned within balloon 216b, secondary cannula 260 is positioned within balloon 216c and balloon 255 is positioned within balloon 216d. Expansion mechanism 245 may be repositioned by contracting balloons 250 and 255, and in some cases secondary cannula 260, and then sliding expansion mechanism 245 along a length of inflation cannula 230 and guidewire cannula 235 such that balloons 250 and 255 are within the balloons of expandable body 218 to be inflated. Once in position, balloons 250 and 255 are inflated and in turn, the overlying balloons of expandable body 218 are inflated. In FIG. 6, inflation of balloon 250 expands balloon 216b and inflation of balloon 255 expands balloon 216d. Balloon 216c remains in an unexpanded state. In this aspect, the treatment agent may now be isolated within a region 602 of vessel 100 between balloons 216b and 216d. It is further contemplated that a pressure within region 602 increases to drive the treatment agent into a wall of vessel 100 within region 602. Balloon 216f remains in an expanded state thus it is further contemplated a pressure within a region of blood vessel 100 between balloon 216d and balloon 216f may further be increased.

FIG. 7 shows the catheter assembly of FIG. 2 with two intermediate expandable members of the catheter assembly expanded. In this embodiment, expansion mechanism 245 is repositioned from that which is shown in FIG. 6 so that balloon 250 is positioned within balloon 216c, secondary cannula 260 is positioned within balloon 216d and balloon 255 is positioned within balloon 216e. As previously discussed, expansion mechanism 245 may be respositioned by contracting balloons 250 and 255, and in some cases secondary cannula 260, and then sliding expansion mechanism 245 along a length of inflation cannula 230 and guidewire cannula 235. Once in position, balloons 250 and 255 may be inflated. In FIG. 7, expansion of balloon 250 expands balloon 216c and expansion of balloon 255 expands balloon 216e. Balloon 216d remains in an unexpanded state. In this aspect, the treatment agent may now be isolated within a region 702 of vessel 100 between balloons 216c and 216e. A pressure created within region 702 due to the inflation of balloons 216c and 216e helps to drive the treatment agent through walls of vessel 100.

Repositioning of expansion mechanism 245 along a length of catheter assembly 200 may continue in this direction until balloon 255 is positioned within balloon 216f. Once balloon 216f is reached, expansion mechanism 245 may be respositioned in an opposite direction toward balloon 216a. In this aspect, the treatment agent may be isolated within regions of vessel 100 multiple times to re-treat regions of vessel 100.

Figure 8:
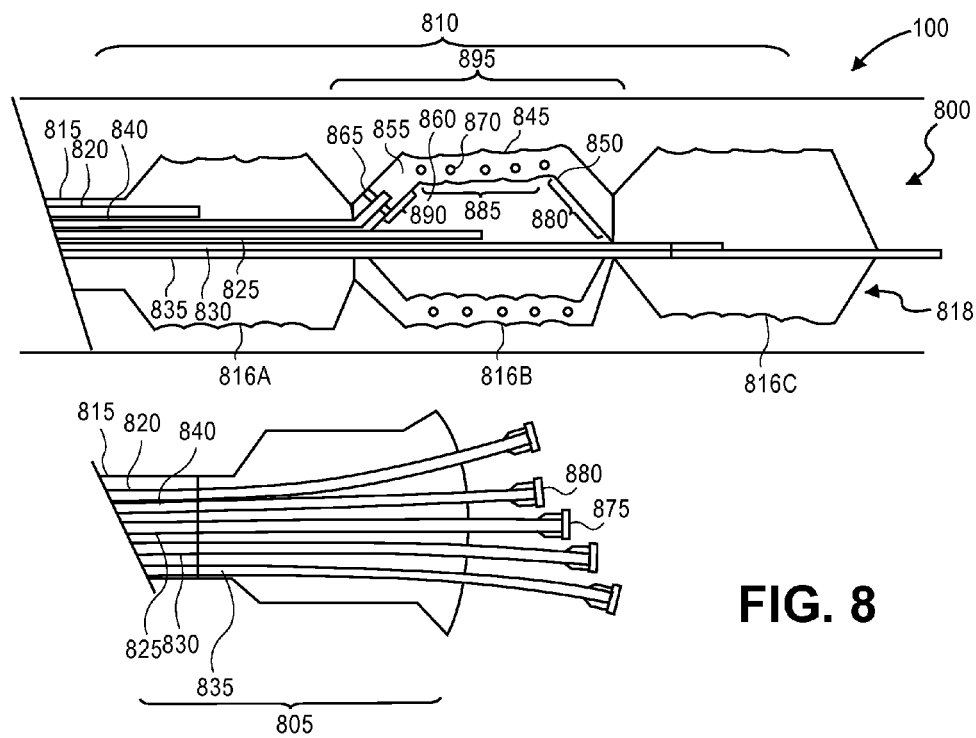
FIG. 8 shows a cross-sectional side view of another embodiment of a catheter assembly to deliver a treatment agent introduced into the blood vessel.

FIG. 8 shows a cross-sectional side view of another embodiment of a catheter assembly to deliver a treatment agent introduced into the blood vessel. FIG. 8 shows blood vessel 100 having catheter assembly 800 disposed therein. Catheter assembly 800 includes proximal portion 805 and distal portion 810. Proximal portion 805 may be external to blood vessel 100 and to the patient. Representatively, catheter assembly 800 may be inserted through a femoral artery and through, for example, a guide catheter and with the aid of a guidewire to a location in the vasculature of a patient. That location may be, for example, a coronary artery. FIG. 8 shows distal portion 810 of catheter assembly 800 positioned along a length of vessel 100.

In one embodiment, catheter assembly 800 includes primary cannula 815 having a length that extends from proximal portion 805 (e.g., located external through a patient during a procedure) to a distal portion 810 to connect with a proximal end of expandable body 818. Expandable body 818 includes expandable members 816a and 816c at each end and a working length 895 including expandable member 816b. Although three expandable members are illustrated in FIG. 8, it is contemplated that any number of expandable members deemed desirable may be used. In this embodiment, expandable members 816a, 816b and 816c are balloons. Balloons 816a, 816b and 816c may be made of a same or different material. It is contemplated that the material of balloons 816a, 816b or 816c may be a porous or non-porous material as deemed desirable. Expandable body 818 having sequentially positioned balloons such as balloons 816a, 816b and 816c may be formed using similar techniques to those described in reference to expandable body 218 shown in the embodiments of FIGS. 2-7. It is further contemplated that the particular specifications of balloons 816a, 816b and 816c are substantially similar to those of balloons of expandable body 218 described in reference to FIGS. 2-7.

Primary cannula 815 connects with a proximal end or skirt of balloon 816a. Primary cannula 815 has a lumen therethrough dimensioned to accommodate inflation cannulas 820, 825, 830, guidewire cannula 835 and delivery cannula 840. Inflation cannula 820 extends from proximal portion 805 of catheter assembly 800 to distal portion 810 and has an end that terminates within balloon 816a. Inflation cannula 830 extends from proximal portion 805 to distal portion 810 and has an end that terminates within balloon 816c. A fluid may be delivered through inflation cannulas 820 and 830 to expand balloons 816a and 816c, respectively. In this aspect, balloons 816a and 816c can be used to occlude vessel 100 and isolate a vessel region between balloons 816a and 816c. Balloons 816a and 816c are inflated to a diameter suitable to occlude vessel 100 without causing damage to the vessel wall.

In some embodiments, inflation cannula 825 and delivery cannula 840 extend from proximal portion 805 of catheter assembly 800 to distal potion 810 and have ends that terminate within balloon 816b. In this embodiment, balloon 816b is a double-walled balloon including an outer balloon wall or membrane 845 and an inner balloon wall or membrane 850. Outer reservoir 855 is formed between outer wall 845 and inner wall 850 and an inner reservoir 860 separate from outer reservoir 855 is defined by inner wall 850. Outer wall 845 and inner wall 850 are attached at one end to a cuff 865 to help maintain separation between outer wall 845 and inner wall 850 so that a distal end of delivery cannula 840 may be inserted between walls 845, 850 and terminate within outer reservoir 855. In one embodiment, cuff 865 may have a cylindrical shape and be of any material suitable for maintaining an opening defined by walls 845, 850 for insertion of delivery cannula 840. In this aspect, a distal end of delivery cannula 840 terminates within outer reservoir 855 and a distal end of inflation cannula 825 terminates within inner reservoir 860 of balloon 816b.

Balloon 816b is selectively inflatable to expand from a collapsed configuration to a desired and controlled expanded configuration. Balloon 816b can be selectively inflated by supplying a fluid or gas into inflation cannula 825 at a rate sufficient to create a pressure through inflation port 875. Alternatively, supplying a fluid into delivery cannula 840 at a rate sufficient to create a pressure through delivery port 880 can be used to selectively expand balloon 816b. In still further embodiments, balloon 816b may be selectively inflated by simultaneously supplying a first fluid or gas into inflation cannula 825 and a second fluid or gas into delivery cannula 840 through ports 875 and 880, respectively. Balloon 816b can further be returned to its collapsed configuration by withdrawing the fluid or gas from outer reservoir 855 or inner reservoir 860 through ports 840 and 825, respectively.

In one embodiment, balloon walls 845 and 850 can be defined by three sections, distal taper wall 880, medial working length 885, and proximal taper wall 890. Distal taper wall 880, medial working length 885, and proximal taper wall 890 of wall 845 may be bound together by seams or be blow-molded of a single seamless material. Similarly, distal taper wall 880, medial working length 885, and proximal taper wall 890 of wall 850 may be bound together by seams or be blow-molded out of a single seamless material. Wall 845 and wall 850 may be connected, such as by molding, at proximal ends to delivery cannula 840, inflation cannulas 825, 830 and guidewire cannula 835 and at distal ends to inflation cannula 830 and guidewire cannula 835. That is, balloon 816*b* may be sealed off from balloons 816*a* and 816*c* so that they are not in fluid communication.

Balloon 816*b* may be made from any suitable material, including, but not limited to, polymers and copolymers of polyolefins, polyamides, polyesters and the like. The specific material employed must be compatible with the fluids or gases employed in conjunction with balloon 816*b* and must be able to stand the pressures that are developed within balloon 816*b*. Balloon walls 845 and 850 may be made of the same or different materials. In one embodiment, balloon wall 845 is made of a material that is permeable to a treatment agent or diagnostic liquids delivered through delivery cannula 840, such as ePTFE. A suitable pore size for an ePTFE balloon material is on the order of one micron (μm) to 60 μms. The porosity of ePTFE material can be controlled to accommodate a treatment agent flow rate or particle size by changing a microstructure of an ePTFE tape used to form a balloon, for example, by wrapping around a mandrel. Alternatively, pore size may be controlled by controlling the compaction process of the balloon, or by creating pores (e.g., micropores) using a laser. In this aspect, pores 870 may be formed along a desired region of balloon 816*b*, such as working length 885 as shown in FIG. 8.

ePTFE as a balloon material is a relatively soft material and tends to be more flexible and conformable with tortuous coronary vessels than conventional balloons. ePTFE also does not need to be folded which will lower its profile and allow for smooth deliverability to distal lesions and the ability to provide therapy to targeted or regional sites post angioplasty and/or stent deployment.

In one embodiment, balloon wall 850 is made of a non-permeable material such as Pebax®, nylon or PET. In some embodiments where balloon wall 845 is a permeable material and balloon wall 850 is a non-permeable material, expansion of balloon 816*b* and delivery of a treatment agent from balloon 816*b* may occur independently of each other. For example, a treatment agent may be introduced into outer reservoir 855 and allowed to permeate through pores 870 of outer wall 845 to a desired vessel region while balloon 816*b* is in an unexpanded state. Once a desired amount of treatment agent passes through wall 845, balloon 816*b* may be inflated by introducing a liquid or gas into inner reservoir 860 through inflation cannula 825. The fluid or gas may be supplied into inflation cannula 825 at a predetermined pressure, for example, between about one and 20 atmospheres. Since vessel 100 is occluded at regions adjacent both ends of balloon 816*b* by balloons 816*a* and 816*c*, expansion of balloon 816*b* increases a pressure within the vessel region surrounding balloon 816*b*. This pressure increase helps to drive the treatment agent through the wall of vessel 100 surrounding balloon 816*b*.

Alternatively, balloon wall 845 and balloon wall 850 may be made of any materials suitable for expansion and delivery of a treatment agent by balloon 816*b*. Balloon walls 845 and 850 may have any thickness so long as the thickness does not unduly compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. An outer diameter and length of inner wall 850 may be less than that of outer wall 845 such that a space is provided for outer reservoir 855 formed between outer wall 845 and inner wall 850. It is appreciated that the specific specifications may vary depending on the procedure for which balloon 816*b* is to be used and the anatomy and size of the target lumen in which balloon 816*b* is to be inserted. For example, in some embodiments, balloon 816*b* may be a single walled balloon and an infusion catheter may be used to deliver the treatment agent.

Catheter assembly 800 also includes guidewire cannula 835 extending, in this embodiment, through expandable body 818 to a distal end of catheter assembly 800. Guidewire cannula 835 has a lumen sized to accommodate a guidewire (not shown). Catheter assembly 800 may be an OTW configuration where guidewire cannula 835 extends from a proximal end (external to a patient during a procedure) to a distal end of catheter assembly 800. Guidewire cannula 835 may also be used for delivery of a treatment agent when the guidewire is removed with catheter assembly 800 in place.

In another embodiment, catheter assembly 800 is a RX-type catheter assembly and only a portion of catheter assembly 800 (a distal portion including expandable body 818) is advanced over the guidewire. In an RX-type of catheter assembly, typically, the guidewire cannula/lumen extends from the distal end of the catheter to a proximal guidewire port spaced distally from the proximal end of the catheter assembly. The proximal guidewire port is typically spaced a substantial distance from the proximal end of the catheter assembly.

Figure 9:
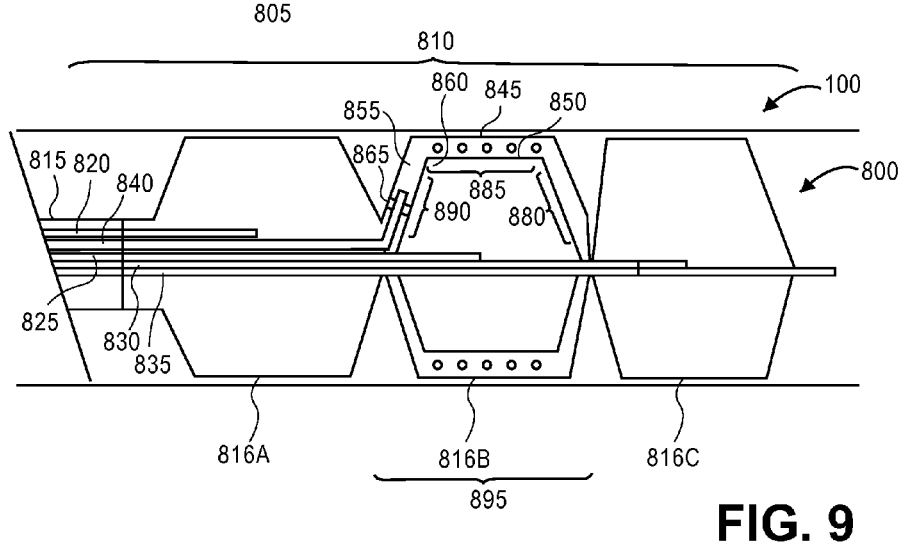
FIG. 9 shows the catheter assembly of FIG. 8 with an intermediate expandable member of the catheter assembly inflated.

In one embodiment, catheter assembly 800 is introduced into blood vessel 100 with expandable body 818 in an unexpanded state as shown in FIG. 8. Once catheter assembly 800 is positioned as desired within vessel 100, for example, adjacent a treatment site, balloons 816*a*, 816*b* and 816*c* are inflated as shown in FIG. 9. Balloons 816*a*, 816*b* and 816*c* may be inflated by introducing a fluid or gas into each balloon through inflation cannulas 820, 825 and 830, respectively. In one embodiment, balloons 816*a*, 816*b* and 816*c* are inflated simultaneously to minimize blood volume within a vessel region adjacent balloons 816*a*, 816*b* and 816*c*. Alternatively, a blood volume may be reduced by partially expanding balloons 816*a* and 816*c* followed by expansion of balloon 816*b* and then fully expanding balloons 816*a* and 816*c* to isolate this region of the vessel. In this aspect, the volume of blood being displaced by expansion of balloon 816*b* is able to escape past balloons 816*a* and 816*c*.

Figure 10:
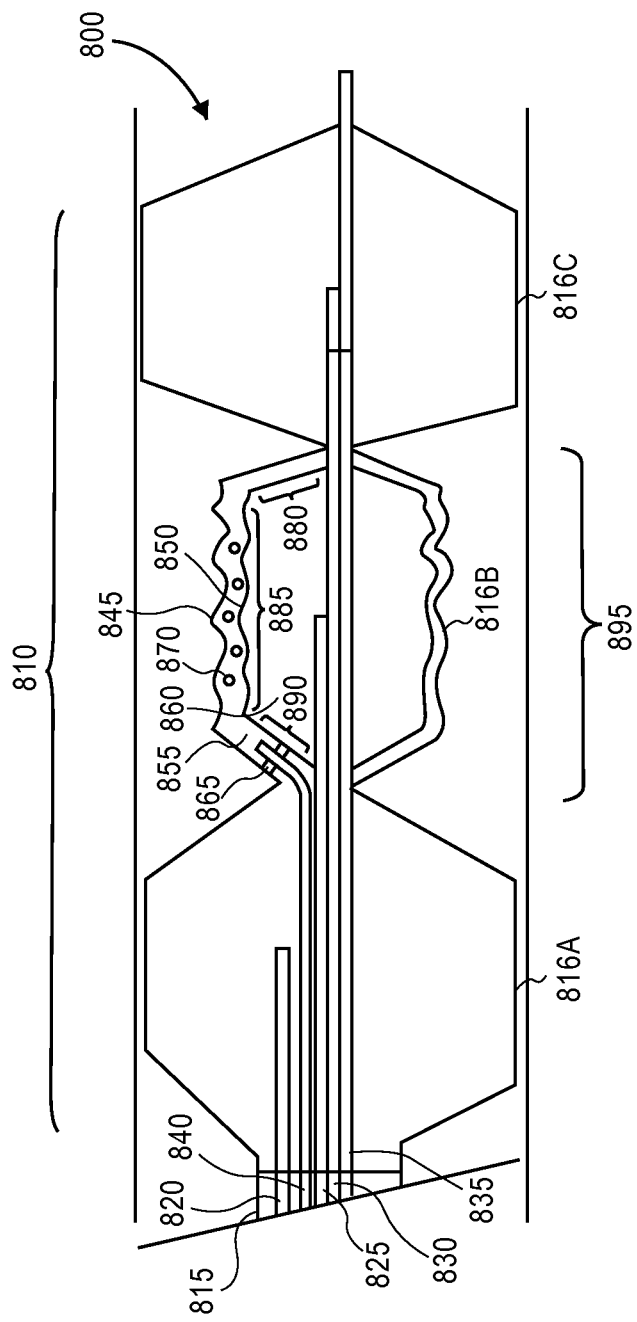
FIG. 10 shows the catheter assembly of FIG. 8 with an intermediate expandable member of the catheter assembly deflated.

Once a blood volume within this region of vessel 100 is reduced, balloon 816*b* is deflated as shown in FIG. 10. Balloon 816*b* may be deflated, by for example, withdrawing the fluid or gas introduced to balloon 816*b* through inflation cannula 825. Balloons 816*a* and 816*b* remain in an expanded state. In this aspect, a region having a reduced blood volume is maintained between balloons 816*a* and 816*b*. The treatment agent, for example, in the form of a solution delivered through delivery cannula 840 to outer reservoir 855. At a relatively low pressure (e.g., on the order of two to four atmospheres (atm)), the treatment agent permeates through pores 870 of outer layer 845 into this low blood volume region of blood vessel 100. Since a minimal amount of blood is within the region between balloons 816*a* and 816*b*, the treatment agent solution is not significantly diluted by blood at the treatment site. In this aspect, the treatment agent concentration in solution is maintained at the treatment site and, in turn, a more concentrated solution of the treatment agent is available for diffusion through the wall of vessel 100 then when the treatment agent solution is delivered to a blood infused vessel region.

In some embodiments, the treatment agent may be introduced to the vessel region simultaneously with balloon 816b contraction. For example, while fluid used to inflate balloon 816b is withdrawn from inner reservoir 860 of balloon 816b through inflation cannula 840, a treatment agent solution is simultaneously delivered to outer reservoir 855 through delivery cannula 840. The treatment agent permeates through pores 870 while balloon 816b is contracting. Once within vessel 100, the treatment agent begins to diffuse through the wall of vessel 100. Diffusion of the treatment agent through the wall of vessel 100 is facilitated by again expanding balloon 816b similar to the configuration shown in FIG. 9. Expansion of balloon 816b increases the pressure within the vessel region between expanded balloons 816a and 816c. This pressure increase drives the treatment agent through the wall of vessel 100.

FIG. 11 shows a cross-sectional side view of another embodiment of a catheter assembly to deliver a treatment agent introduced into the blood vessel. FIG. 11 shows blood vessel 100 having catheter assembly 1100 disposed therein. Catheter assembly 1100 includes proximal portion 1105 and distal portion 1110. Proximal portion 1105 is external to blood vessel 100 and to the patient. Representatively, catheter assembly 1100 may be inserted through a femoral artery and through, for example, a guide catheter and with the aid of a guidewire to a location in the vasculature of a patient. In some embodiments, that location is a coronary artery. FIG. 11 shows distal portion 1110 of catheter assembly 1100 positioned along a length of vessel 100.

In one embodiment, catheter assembly 1100 includes primary cannula 1115 having a length that extends from proximal portion 1105 (e.g., located external through a patient during a procedure) to distal portion 1110. One end of primary cannula 1115 connects to a proximal end of expandable body 1118. In this embodiment, expandable body 1118 includes an elongated body 1120 having expandable members 1116a and 1116c at each end. In some embodiments, elongated body 120 is an elongated balloon and expandable members 1116a and 1116c are ends of the balloon. Expandable body 1118 further includes an intermediate expandable member 1116b movably positioned along a working length 1112 of expandable body 1118. In this embodiment, intermediate expandable member 1116b is an inflatable cuff, for example, a cuff shaped balloon positioned around working length 1112 of expandable body 1118. In this aspect, inflatable cuff 1116b constricts a region of the working length of elongated body 1120 such that when elongated body 1120 is inflated, expandable members 1116a and 1116b expand while the region constricted by inflatable cuff 1116b maintains a diameter less than that of expandable members 1116a and 1116c. A peristaltic motion may be achieved in this embodiment by inflation of expandable body 1118 with inflatable cuff 1116b at a first position along working length 1112 and then moving inflatable cuff 1116b to a second different position along working length 1112. This motion may continue until an end of expandable body 1118 is reached. Additionally, a region of vessel 100 having a reduced blood volume may be isolated as described in reference to FIGS. 2-10 by inflating expandable members 116a, 116b and 116c simultaneously and then deflating intermediate expandable member 116b while expandable members 116a and 116c remain expanded.

Expandable members 1116a and 1116c are used to occlude vessel 100 and anchor expandable body 1118 in place within vessel 100. In this aspect, elongated body 1120 of expandable body 1118 and in turn expandable members 1116a and 1116c are made of a material suitable for anchoring expandable body 1118 within vessel 100, such as an elastomeric material. Additionally, elongated body 1120 of expandable body 1118 may be of a material or include a coating along its surface to facilitate sliding of inflatable cuff 1116b along working length 1112 of expandable body 1118. Representatively, elongated body 1120 includes a polytetrafluoroethylene (PTFE) coating applied to the surface of elongated body 1120 by any suitable technique. Inflatable cuff 1116b may be made of a similar or different, e.g., less compliant, material with our without a coating. Suitable materials include, but are not limited to, non-permeable materials such as Pebax®, nylon or polyethylene terephthalate (PET). Alternatively, expandable members 1116a, 1116b and 1116c are made of a porous material such as extended polytetrafluoroethylene (ePTFE) to allow for delivery of a treatment agent through pores of the expandable members. In some embodiments, elongated body 1120 of expandable body 1118 and inflatable cuff 1116b may be formed separately by a blow-molding process of a single seamless material. Alternatively, any other suitable technique may be used to form elongated body 1120 of expandable body 1118 and inflatable cuff 1116b.

Regardless of the technique used for forming expandable body 1118, it is desired that a shape of elongated body 1120 accommodate various cannulas attached to inflatable cuff 1116b. For example, in some embodiments secondary inflation cannula 1122, wires 1124a, 1124b and delivery cannula 1130 are attached to inflatable cuff 1116b as shown in FIG. 12 and extend along an outer surface of elongated body 1120. In this aspect, elongated body 1120 includes recesses 1202 and 1204 as shown in FIG. 12 to accommodate secondary inflation cannula 1122, wires 1124a, 1124b and delivery cannula 1130 therein. The dimensions of recesses 1202 and 1204 and their location around the periphery of elongated body 1120 may vary as deemed desirable.

A size and shape of expandable members 1116a, 1116b and 1116c may vary. Although, substantially tubular members with a circular cross-section are illustrated in FIG. 11, it is contemplated that the expandable members may be any other shape deemed desirable. A suitable diameter for expandable body 1118 is, for example, in the range of two to five millimeters (mm), a length may be on the order of eight to 60 mm or more depending upon the desired treatment region and the profile range is, for example, approximately 0.030 inches to 0.040 inches or more.

Primary cannula 1115 connects with a proximal end or skirt of expandable member 1116a. Primary cannula 1115 has a lumen therethrough dimensioned to accommodate inflation cannula 1126, guidewire cannula 1128, wires 1124a and 1124b, secondary inflation cannula 1122, and delivery cannula 1130 therein. Secondary inflation cannula 1122 extends from proximal portion 1105 of catheter assembly 1100 to distal portion 1110 and has an end that terminates within inflatable cuff 1116b positioned around elongated body 1120 of expandable body 1118. Inflation cannula 1126 extends from proximal portion 1105 to distal portion 1110 and has an end that terminates within expandable member 1116a of elongated body 1120. In this aspect, expandable members 1116a and 1116c may be inflated and in turn used to occlude vessel 100 by delivering, for example, a fluid, through inflation cannula 1126 of elongated body 1120. In one embodiment, elongated body 1120 and, in turn, expandable members 1116a and 1116c have dimensions such that each balloon may be inflated to a diameter suitable to occlude vessel 100 without causing damage to the vessel wall.

Delivery cannula 1130 extends from proximal portion 1105 of catheter assembly 1100 to distal portion 1110. Delivery cannula 1130 extends along elongated body 1120 through one side of inflatable cuff 1116b and terminates at a surface of inflatable cuff 1116b which is not in contact with elongated body 1120. An outlet port 1132 of delivery cannula 1130 is positioned at an outer surface of elongated body 1120. In this aspect, a treatment agent may be delivered through delivery cannula 1130 and into isolated region 1134 of vessel 100 through outlet port 1132 of delivery cannula 1130. Although delivery cannula 1130 is shown, it is further contemplated that other mechanisms suitable for delivering a treatment agent to region 1134 may be used as deemed desirable.

Secondary inflation cannula 1122 extends from proximal portion 1105 of catheter assembly 1100 to distal portion 1110. Secondary inflation cannula 1122 extends along elongated body 1120 and terminates within inflatable cuff 1116b. In this aspect, a fluid, for example, may be delivered through secondary inflation cannula 1122 and into inflatable cuff 1116b to inflate inflatable cuff 1116b. It is contemplated that inflation of inflatable cuff 1116b after delivery of the treatment agent to region 1134 will help to drive the treatment agent through the wall of vessel 100 adjacent within this region.

Wires 1124a and 1124b extend from proximal portion 1105 of catheter assembly 1100 to distal portion 1110. Wires 1124a and 1124b extend along an outer surface of a wall of elongated body 1120 and are secured to a surface of inflatable cuff 1116b to facilitate sliding of inflatable cuff 1116b along elongated body 1120. For example, when it is desired to move cuff 1116b to a different position along elongated body 1120, wires 1124a and 1124b may be partially withdrawn from catheter assembly 1100 to move inflatable cuff 1116b to a position to the left of that which is shown in FIG. 11 or advanced farther into catheter assembly 1100 to move inflatable cuff 1116b to a position to the right of to that which is shown in FIG. 11. By moving inflatable cuff 1116b in this manner, isolated region 1134 and, in turn, a treatment agent within isolated region 1134, may be moved to different regions along vessel 100 where treatment is desired. Wires 1124a and 1124b may be of a same or different material suitable for moving inflatable cuff 116b as described herein. Representative materials for wires 1124a and 1124b include, but are not limited to, stainless steel, tungsten, other metals or metal alloys and the like. Although wires 1124a and 1124b are shown, it is further contemplated that other mechanisms suitable for moving inflatable cuff 1116b along elongated body may be used as deemed desirable.

Catheter assembly 1100 also includes guidewire cannula 1128 extending, in this embodiment, through elongated body 1120 of expandable body 1118 to a distal end of catheter assembly 1100. Guidewire cannula 1128 has a lumen sized to accommodate a guidewire 1127 to facilitate insertion of catheter assembly 1100 into vessel 100. Catheter assembly 1100 may be an OTW configuration where guidewire cannula 1100 extends from a proximal end (external to a patient during a procedure) to a distal end of catheter assembly 1100. In some embodiments, guidewire cannula 1128 may also be used for delivery of a treatment agent to a region upstream from catheter assembly 1100 when guidewire 1127 is removed with catheter assembly 1100 in place.

In another embodiment, catheter assembly 1100 is a RX-type catheter assembly and only a portion of catheter assembly 1100 (a distal portion including expandable body 1118) is advanced over the guidewire. In a RX-type of catheter assembly, typically, the guidewire cannula extends from the distal end of the catheter to a proximal guidewire port spaced distally from the proximal end of the catheter assembly. The proximal guidewire port is typically spaced a substantial distance from the proximal end of the catheter assembly.

In one embodiment, catheter assembly 1100 is introduced into blood vessel 100 in a deflated state and once in position, inflated (e.g., with a suitable liquid through inflation cannula 1126) to occlude blood vessel 100 and isolate a vessel region within working length 1112. In some embodiments, inflatable cuff 1116b is placed adjacent to a treatment site such that expandable members 1116a and 1116c are positioned on opposite sides of the treatment site. Upon inflation, blood flow is prevented from flowing into region 1134. Following occlusion, a solution (fluid) of the treatment agent is introduced through delivery cannula 1130 to isolated vessel region 1134. In this aspect, a treatment agent delivered within region 1134 is isolated at the treatment site. Inflatable cuff 1116b may be inflated to increase a pressure within region 1134, thereby driving the treatment agent through the wall of vessel 100 within region 1134. It is further noted that inflatable cuff 1116b includes separate inflation and delivery cannulas such that treatment agent delivery is independent from inflation of inflatable cuff 1116b.

FIG. 12 shows a cross-sectional front view of the catheter assembly of FIG. 11. In this embodiment, a cross-sectional front view through line 12-12' of expandable body 1118 is shown. Inflatable cuff 1116b is positioned around elongated body 1120. As shown, secondary inflation cannula 1122 and wire 1124a are positioned within recess 1202 and wire 1124b and delivery cannula 130 are positioned within recess 1204. In this aspect, secondary inflation cannula 1122, wires 1124a and 1124b and delivery cannula 130 slide along the surface of elongated body 1120 within recesses 1124a and 1124b as inflatable cuff 1116b is moved along elongated body 1120. Inflation cannula 1126 and guidewire cannula 1128 with wire 1127 disposed therein are shown positioned within elongated body 1120.

Figure 13:
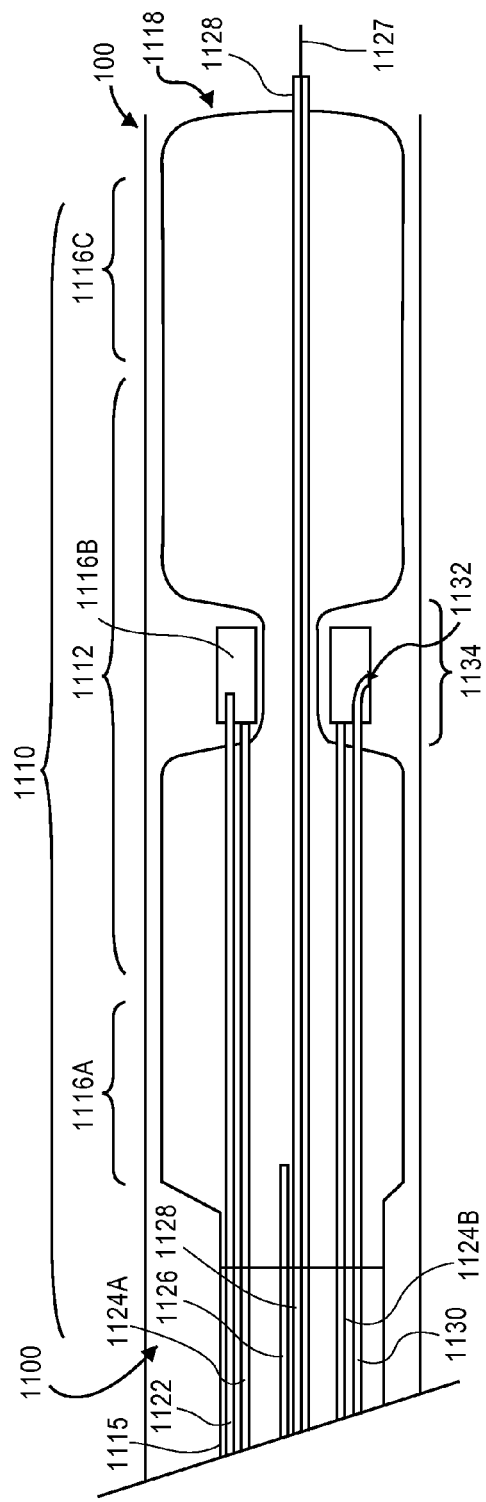
FIG. 13 shows the catheter assembly of FIG. 11 with an inflatable cuff repositioned from that which is shown in FIG. 11.

FIG. 13 shows the catheter assembly of FIG. 11 with an inflatable cuff repositioned from that which is shown in FIG. 11. Catheter assembly 1100 includes substantially the same components as that described in reference to FIG. 13. In this embodiment, only a distal portion 1110 of catheter assembly 1100 positioned within vessel 100 is shown. In this embodiment, inflatable cuff 1116b is shown to the right of that which is shown in FIG. 11 such that region 1302, also to the right of region 1134 shown in FIG. 11, is now isolated. In this aspect, the treatment agent may now be isolated within region 1302 of vessel 100. A pressure within isolated region 1302 of vessel 100 may then be increased by inflating inflatable cuff 1116b to help drive the treatment agent through walls of vessel 100.

Repositioning of inflatable cuff 1116b along a length of elongated body 1120 may continue in this direction until inflatable cuff 1116b reaches an end of elongated body 1120. Once an end of elongated body 1120 is reached, inflatable cuff 1116b may be respositioned in an opposite direction toward expandable member 1116a. In this aspect, the treatment agent may be isolated within regions of vessel 100 multiple times to re-treat regions of vessel 100.

The above delivery devices and systems are representation of devices that may be used to deliver a treatment agent including, but not limited to, a treatment agent capable of reducing the likelihood of restenosis. For example, an anti-inflammatory agent may be introduced and isolated to a desired treatment site with a variety of delivery devices. These devices include balloons of an expandable body sequentially inflated to produce a peristaltic motion along a length of the vessel. The devices further include balloons of an expandable body that are inflated to reduce a blood volume and subsequently increase a pressure within a region of treatment agent delivery. Additional delivery devices may further be used, for example, an electrical delivery device capable of producing a peristaltic motion that may be used to isolate the treatment agent to different segments of the vessel. In addition, it is contemplated that the devices described herein may be used in combination with a perfusion catheter to allow an amount of blood to be delivered to the isolated region during a treatment procedure.

In the preceding detailed description, reference is made to specific embodiments thereof. It will, however, be evident that various modifications and changes may be made thereto without departing from the broader spirit and scope of the following claims. The specification and drawings are, accordingly, to be regarded in an illustrative rather than a restrictive sense.

What is claimed is:

1. An apparatus comprising:
   a primary cannula having a dimension suitable for insertion into a blood vessel;
   a first expandable body coupled to the primary cannula, the first expandable body comprising a first expandable member and a second expandable member to isolate a length of the vessel upon expansion within the blood vessel and a working length between the first expandable member and the second expandable member comprising a plurality of longitudinally spaced intermediate expandable members, wherein the plurality of intermediate expandable members may be expanded separate from an expansion of the first expandable member and the second expandable member; and
   an expansion mechanism comprising a second expandable body movably disposed within the first expandable body to facilitate expansion of the plurality of expandable members, wherein the second expandable body comprises a first balloon and a second balloon attached to opposite ends of a secondary cannula, and wherein the secondary cannula comprises a length dimension substantially similar to a length of one of the plurality of intermediate expandable members such that the first balloon and the second balloon are disposed within, and facilitate expansion of, every other one of the plurality of intermediate expandable members.

2. The apparatus of claim 1, wherein each of the first expandable member and the plurality of intermediate expandable members comprise a balloon.

3. The apparatus of claim 1, further comprising:
   a delivery cannula coupled to the first expandable member and terminating within the isolated length of the blood vessel to facilitate delivery of a treatment agent.

4. The apparatus of claim 1, wherein the secondary cannula is disposed within a portion of the working length of the first expandable body.

5. The apparatus of claim 4, further comprising at least one inflation cannula configured to inflate or deflate the at least one balloon separate from an inflation or deflation of the first expandable body.

6. A kit comprising:
   a primary cannula having a dimension suitable for insertion into a blood vessel, a first expandable body coupled to the primary cannula and an expansion mechanism comprising a second expandable body movably disposed within the first expandable body, the first expandable body comprising a first expandable member and a second expandable member to isolate a length of the vessel upon expansion within the blood vessel and a working length between the first expandable member and the second expandable member comprising a plurality of longitudinally spaced intermediate expandable members wherein the plurality of intermediate expandable members may be expanded separate from an expansion of the first expandable member and the second expandable member using the expansion mechanism, wherein the second expandable body comprises a first balloon and a second balloon attached to opposite ends of a secondary cannula, and wherein the secondary cannula comprises a length dimension substantially similar to a length of one of the plurality of intermediate expandable members such that the first balloon and the second balloon are disposed within, and facilitate expansion of, every other one of the plurality of intermediate expandable members; and
   a treatment agent for delivery to a treatment site within the length of vessel between the first expandable member and the second expandable member.

7. The kit of claim 6, wherein each of the first expandable member and the plurality of intermediate expandable members comprise a balloon.

8. The apparatus of claim 6, further comprising at least one inflation cannula configured to inflate or deflate the first balloon or the second balloon separate from an inflation or deflation of the first expandable body.

9. An apparatus comprising:
   a cannula having dimensions suitable for insertion into a blood vessel;
   a first expandable body coupled to the cannula, the first expandable body comprising a plurality of expandable members longitudinally spaced along a length of the cannula, wherein the plurality of expandable members are independently expandable such that adjacent regions along a length of the blood vessel are isolated between the expandable members; and
   an expansion mechanism comprising a second expandable body movably disposed within the first expandable body to facilitate expansion of the plurality of expandable members, wherein the second expandable body comprises a first balloon and a second balloon attached to opposite ends of a secondary cannula, and wherein the secondary cannula comprises a length dimension substantially similar to a length of one of the plurality of expandable members such that the first balloon and the second balloon are disposed within, and facilitate expansion of, every other one of the plurality of expandable members.

* * * * *